United States Patent [19]

Wu

[11] Patent Number: 5,227,562
[45] Date of Patent: Jul. 13, 1993

[54] ETHYLENE DIMERIZATION

[75] Inventor: An-hsiang Wu, Bartlesville, Okla.

[73] Assignee: Phillips Petroleum Company, Bartlesville, Okla.

[21] Appl. No.: 833,277

[22] Filed: Feb. 10, 1992

[51] Int. Cl.$^5$ ............................ C07C 2/08; C07C 2/32
[52] U.S. Cl. .................................... 585/520; 585/510;
585/511; 585/514; 585/521; 585/531; 502/325
[58] Field of Search ............... 585/510, 511, 514, 520, 585/521, 531

[56] References Cited

U.S. PATENT DOCUMENTS

| | | | |
|---|---|---|---|
| 3,829,429 | 8/1974 | Clement | 260/290 P |
| 3,855,255 | 12/1974 | Dohr et al. | 260/10.9 R |
| 3,904,692 | 9/1975 | Lassau et al. | 260/586 P |
| 4,716,138 | 12/1987 | Murray | 502/117 |
| 4,731,490 | 3/1988 | Coughenour et al. | 568/697 |

OTHER PUBLICATIONS

Hata, Go, "A New Catalyst System for the Dimerization of Ethylene", *Chemistry and Industry* (Jan. 30, 1965), p. 223.

*Primary Examiner*—Asok Pal
*Assistant Examiner*—P. Achutamurthy
*Attorney, Agent, or Firm*—William R. Sharp

[57] ABSTRACT

An ethylene dimerization process is provided wherein ethylene is contacted with an organocobalt(II) or organocobalt(III) compound and a borohydride compound in a solvent to produce a product reaction mixture comprising a $C_4$ fraction of predominantly 1-butene. A phosphine compound can additionally be provided in the solvent with an organocobalt(III) compound to enhance selectivity to 1-butene.

19 Claims, No Drawings

ETHYLENE DIMERIZATION

This invention relates to a process for dimerizing ethylene to butenes, comprising predominantly 1-butene.

1-butene, along with other α-olefins or 1-olefins, has become a very important product in the chemical industry. Through hydroformylation, copolymerization and arylation/sulfonation, 1-butene can become a component of plasticizers, solvents, plastics, surfactants, synthetic lubricants, fatty acids and detergents. Production of 1-butene by dimerizing ethylene has been previously investigated to a considerable extent, but further improvement would be desirable in regard to achieving a combination of high productivity and high selectivity to 1-butene.

It is, therefore, an object of the invention to provide an improved process for dimerizing ethylene which achieves the above-mentioned combination of results.

The above object is achieved by a process for dimerizing ethylene to butenes comprising: contacting ethylene, a cobalt compound selected from the group consisting of an organocobalt(II) compound and an organocobalt(III) compound (where II and II indicate cobalt valence states of +2 and +3, respectively), and a borohydride compound of the formula $MBH_{4-n}R_n$ where $n=1$, 2 or 3, M is an alkali metal and each R independently represents a $C_1$ to $C_{20}$ hydrocarbyl radical, and wherein the ethylene is in a gaseous phase and the cobalt compound and borohydride compound are in a solvent and in a liquid phase, thereby producing a product reaction mixture in a liquid phase comprising said butenes. When an organocobalt(III) compound is employed in the process, it is desirable that a phoshpine compound is also present in the solvent to enhance selectivity to 1-butene. Such a phosphine compound is of the formula $PR'_3$ where R' independently represents H or a $C_1$ to $C_{20}$ hydrocarbyl radical and where at least one R' is not H.

Suitable organocobalt(II) compounds include bis(cyclopentadienyl)cobalt(II), cobalt(II) acetylacetonate, cobalt(II) cyclohexanebutyrate, cobalt(II) oxalate, cobalt(II) phthalocyanine, cobalt(II) stearate, cobalt(II) meso-tetramethoxyphenylporphine and cobalt(II) meso-tetraphenylporphine. Bis(cyclopentadienyl)cobalt(II) and cobalt(II) acetylacetonate are preferred, but cobalt(II) acetylacetonate is particularly preferred.

Suitable organocobalt(III) compounds include cobalt(III) acetylacetonate, cobalt(III) sepulchrate trichloride and cobalt(III) sepulchrate tris(tetraphenylborate). Cobalt(III) acetylacetonate is preferred.

The cobalt compound can be in either hydrated or essentially anhydrous form, but the essentially anhydrous form is preferred due to the tendency of water to react with the borohydride compound and interfere with the dimerization process. In this regard, it is desirable to dehydrate any cobalt compound by any suitable technique (such as the refluxing technique described in subsequent examples) immediately prior to its use in the dimerization process, whether or not the cobalt compound is commercially available as "anhydrous" or "hydrated". Even cobalt compounds available from commercial suppliers as "anhydrous" will tend to absorb some moisture when exposed to air for a period of time. It is most preferred that the cobalt compound is dehydrated to a state in which the compound has less than about 1 weight percent water.

Suitable borohydrides of the formula $MBH_{4-n}R_n$ (where $n=1$, 2 or 3, M is an alkali metal such as sodium, potassium or lithium, and each R independently represents a $C_1$ to $C_{20}$ hydrocarbyl radical) include sodium triethylborohydride, sodium tri-sec-butylborohydride, potassium tri-sec-butylborohydride, potassium triethylborohydride, potassium triphenylborohydride, potassium trisiamylborohydride, lithium thexylborohydride, lithium dimethylborohydride, lithium thexyllimonylborohydride, lithium triethylborohydride and lithium tri-sec-butylborohydride. Particularly preferred in accordance with the invention are those borohydrides of the above-mentioned formula where $n=3$ and R is a $C_1$ to $C_{12}$, preferably $C_1$ to $C_6$, alkyl radical. Sodium triethylborohydride is most preferred.

As discussed above, a phosphine compound can be employed in conjunction with the organonickel(III) compound to enhance selectivity to 1-butene. Suitable phosphine compounds of the formula $PR'_3$, where R' independently represents H or a $C_1$ to $C_{20}$ hydrocarbyl radical and where at least one R' is not H, include cyclohexylphosphine, dicyclohexylphosphine, tricyclohexylphosphine, triethylphosphine, triisopropylphosphine, triisobutylphosphine. tri-n-butylphosphine, tri-t-butylphosphine, diphenylphosphine, triphenylphosphine, diphenylcyclohexylphosphine, diethylphenylphosphine, ortho-tolyldiphenylphosphine, di(orthotolyl)phenylphosphine and tribenzylphosphine.

With respect to molar ratios of the various reagents discussed above, the molar ratio of the borohydride compound to the organocobalt(II) compound is preferably about 1–10 to 1 and most preferably about 1.5–2.5 to 1, whereas the molar ratio of the borohydride compound to the organocobalt(III) compound is preferably about 2–10 to 1 and most preferably about 2.5–3.5 to 1. Where the phosphine compound is used in conjunction with the organocobalt(III) compound, the molar ratio of the phosphine compound to the organocobalt(III) compound is preferably about 0.1–20 to 1, most preferably about 1–6 to 1 to achieve a desirable balance of productivity and selectivity to 1-butene. As will be demonstrated in a subsequent example, increasing the molar ratio of the phosphine compound to the organonickel(III) compound generally increases the selectivity to 1-butene but decreases productivity.

The solvent is selected from the group consisting of: at least one saturated hydrocarbon of the formula $C_nH_{2n+2}$ where $n=4$, 5, 6, 7 or 8; at least one aromatic hydrocarbon of the formula $C_6H_{6-n}(R'')_n$ where $n=0$, 1, 2, 3 or 4 and each R'' independently represents a $C_1$ to $C_6$ alkyl radical; and mixtures thereof. Suitable saturated hydrocarbons include isobutane, isopentane, neohexane, n-heptane, n-pentane, octane and isooctane. Suitable aromatic hydrocarbons include benzene, toluene, ethylbenzene, xylene (o,p,m), cumene, isobutylbenzene and t-butylbenzene. The aromatic hydrocarbons are preferred.

The weight ratio of the solvent to the combination of the cobalt compound, borohydride compound, and optionally the phosphine compound if used in conjunction with an organocobalt(III) compound, can be in the broad range of about $1-10^6$ to 1, most preferably in the range of about 5–10,000 to 1. The amount of solvent employed depends upon the cost, ease of product recovery therefrom, reactor size and other practical considerations.

The particular procedure by which the various reagents are contacted can take a variety of forms as should be apparent to one skilled in the art. According to a preferred procedure, the cobalt compound can first be added with the solvent (and also optionally with the phosphine compound if used in conjunction with an organocobalt(III) compound) in a liquid phase to a vessel such as an autoclave or other similar pressure reactor, and a solution of the borohydride compound subsequently added to the vessel in the presence of gaseous ethylene at a pressure specified below. The liquid phase is preferably agitated during contacting with the ethylene.

Pressure and temperature conditions are such that the ethylene is in a gaseous phase and the cobalt compound, borohydride compound, and optionally the phosphine compound as in the solvent are in the liquid phase. More specifically, the process is preferably carried out at a pressure of about 5 to about 5000 psig and a temperature of about 0° C. to about 125° C., most preferably at a pressure of about 200 to about 1000 psig and a temperature of about 20° C. to about 50° C.

The process is preferably carried out for a time of about 1 minute to about 15 hours, most preferably about 15 minutes to about 5 hours.

The butenes as contained in the product reaction mixture can be separated and recovered from the product reaction mixture by conventional means such as fractional distillation. As demonstrated in examples to follow, such butenes comprise predominantly 1-butene.

Many variations of the invention are possible in light of the above teachings. For example, although the invention is described above in terms of a batchwise process, it is within the scope of certain broad aspects of the invention to employ a continuous process wherein ethylene is passed continuously into a reaction zone while product reaction mixture containing the butenes is concomitantly withdrawn therfrom.

Examples are set forth below which further illustrate the invention but which should not be construed to limit the invention in any manner.

Each example employed a 300 mL stainless steel (316SS) Autoclave Engineers stirred tank autoclave, hereafter denoted simply as a reactor. Other equipment employed in individual examples will be referenced in those examples. It is understood that the contents of such reactor in the following examples are being agitated, typically at a slow agitation of about 300 rpm during purging of the reactor or addition or various reagents to the reactor, and at a normal agitation of about 1600 rpm at all other times.

Product analysis was performed on approximately 5 gram samples with an HP 5890 II GC-FID Spectrometer equipped with a capillary DB-1 (60 m) column. The column was operated at 30° C for 5 minutes, followed by a 15° C./minute increase to 285° C. which was held for 13 minutes. Detection was obtained using a flame ionization detector in the area percent mode. Selectivity and weight percent distribution, discussed further below, were determined from spectra as recorded by the spectrometer.

In the following examples, results are reported in terms of productivity, weight percent $C_4$ and selectivity to 1-butene, trans-2-butene and cis-2-butene. Productivity is defined as the grams of oligomerization product (olefinic oligomers of ethylene, i.e. $C_nH_{2n}$, or simply "$C_n$", where n=4,5 ...) produced per gram of Co per hour, and was calculated in each example based on grams of ethylene reacted. Weight percent $C_4$ is the weight percent of the dimer $C_4$ of the total oligomerization product. Selectivity to 1-butene, trans-2-butene and cis-2-butene is given in terms of the weight percent of the total $C_4$ fraction.

EXAMPLE I

This example demonstrates dimerization of ethylene in accordance with the invention employing cobalt(II) acetylacetonate and sodium triethylborohydride in various aromatic solvents.

Cobalt(II) acetylacetonate in essentially anhydrous form was first produced from commercially available cobalt(II) acetylacetonate hydrate. A suspension of the cobalt(II) acetylacetonate hydrate (about 10 g) and toluene (200 mL) was heated to reflux under nitrogen atmosphere with agitation for 24 hours. Water was accordingly refluxed into a Dean-Stark trap. The resulting mixture was then filtered in a nitrogen atmosphere and dried in vacuo for a period of between 1 and 2 hours to give the anhydrous cobalt(II) acetylacetonate.

A reactor was purged with nitrogen for about 5 minutes followed by addition of 50 mL of a freshly distilled aromatic solvent specified in Table I and a sample of the above produced anhydrous cobalt(II) acetylacetonate (0.257 g; 1.00 mmol). The reactor was immediately sealed, purged with ethylene 4-6 times, and then pressured to 50 psig with ethylene at ambient temperature (about 25° C.) for 5 minutes.

To a 40 mL addition vessel, connected to the reactor through an addition valve, was added 2 mL of a 1.0M solution of sodium triethylborohydride (2.0 mmol) in toluene by means of a syringe. The addition vessel was immediately sealed and pressured to 700 psig with ethylene. The contents of the addition vessel, including the ethylene, were then transferred to the reactor through the addition valve at the end of the above-mentioned 5 minute period. Reaction proceeded immediately as evidenced by the rise in reaction temperature. The reaction temperature was controlled at the temperature (Rx Temp. in °C.) indicated in Table I by use of external cooling water. The internal reactor pressure was maintained at 700 psig and the reaction was continued for a time (Rx time in minutes) also indicated in Table I.

At the end of the reaction period, a sample of the product reaction mixture was taken from the reactor through its sample valve into a 50 mL pressure sample tube, and was analyzed as described above. The resulting selectivities and weight percent $C_4$ data, along with corresponding solvent and productivity, are set forth in Table I.

TABLE I

| Run | Solvent | Rx Temp. | Rx Time | Productivity | Wt. % $C_4$ | Selectivity wt. % 1-, trans-2-, cis-2-butene |
|---|---|---|---|---|---|---|
| 1 | Benzene | 38 | 60 | 876 | 99 | 90,8,2 |
| 2 | Toluene | 39 | 30 | 1224 | 98 | 86,12,2 |
| 3 | p-Xylene | 37 | 30 | 1044 | 99 | 91,7,2 |
| 4 | o-Xylene | 37 | 30 | 1255 | 99 | 92,7,1 |
| 5 | m-Xylene | 40 | 30 | 1317 | 98 | 92,7,1 |

TABLE I-continued

| Run | Solvent | Rx Temp. | Rx Time | Productivity | Wt. % C$_4$ | Selectivity wt. % 1-, trans-2-, cis-2-butene |
|---|---|---|---|---|---|---|
| 6 | Ethylbenzene | 41 | 60 | 1542 | 98 | 89,9,2 |
| 7 | Cumene | 40 | 60 | 1488 | 98 | 92,6,2 |
| 8 | Isobutylbenzene | 40 | 60 | 1425 | 99 | 92,7,1 |
| 9 | t-Butylbenzene | 40 | 60 | 1281 | 99 | 92,7,1 |

The results of Table I indicate a weight percent of C$_4$ of the total oligomerization product to be at least 98 weight percent, and a selectivity to 1-butene of at least 86% but generally over 90%. Table I also indicates generally high productivities, with a productivity of over 1500 g/g/hr obtained in run 6.

EXAMPLE II

This example demonstrates ethylene dimerization employing different phosphine compounds at different molar ratios of the phosphine compound to cobalt(III) acetylacetonate.

The cobalt(III) acetylacetonate employed in this example was in essentially anhydrous form. Cobalt(III) acetylacetonate commercially available as anhydrous was nevertheless subjected to the same dehydration procedure described in Example I to ensure removal of any water which might have been absorbed by the commercially available sample.

The runs of this example were carried out similarly to the runs of Example I except for the following: toluene was used as the aromatic solvent in each run; 3 mL of the solution of sodium triethylborohydride (3.0 mmol) in toluene was used instead of 2 mL; anhydrous cobalt(III) acetylacetonate (0.356 g; 1.00 mmol) was used instead of anhydrous cobalt(II) acetylacetonate; and a phosphine compound indicated in Table II was also added to the reactor with the anhydrous cobalt(III) acetylacetonate at indicated molar ratios to the anhydrous cobalt(III) acetylacetonate of 1:1 to 6:1 in runs 11–28, whereas run 10 was a control run using no phosphine compound. Table II utilizes a notation wherein the phosphine compound employed in a series of runs is indicated only for the first run of such series (i.e., runs 11–16 used triphenylphosphine).

TABLE II

| Run | Phosphine | M. Ratio[a] | Rx Temp. | Rx Time | Productivity | Wt. % C$_4$ | Selectivity wt. % 1-, trans-2-, cis-2-butene |
|---|---|---|---|---|---|---|---|
| 10 | None | N/A | 40 | 30 | 3390 | 99 | 70,25,5 |
| 11 | TPP[b] | 1:1 | 40 | 30 | 2628 | 98 | 76,20,4 |
| 12 | | 2:1 | 40 | 30 | 2331 | 99 | 84,13,3 |
| 13 | | 3:1 | 39 | 60 | 1850 | 98 | 88,10,2 |
| 14 | | 4:1 | 40 | 60 | 1347 | 99 | 92,7,1 |
| 15 | | 5:1 | 40 | 60 | 1054 | 99 | 94,5,1 |
| 16 | | 6:1 | 39 | 60 | 954 | 99 | 95,4,1 |
| 17 | TCP[c] | 1:1 | 38 | 30 | 2055 | 98 | 80,16,4 |
| 18 | | 2:1 | 40 | 30 | 1530 | 99 | 84,13,3 |
| 19 | | 3:1 | 40 | 60 | 1260 | 99 | 88,10,2 |
| 20 | | 4:1 | 40 | 60 | 1052 | 99 | 91,7,2 |
| 21 | | 5:1 | 40 | 60 | 845 | 99 | 93,6,1 |
| 22 | | 6:1 | 39 | 60 | 682 | 99 | 95,4,1 |
| 23 | TBP[d] | 1:1 | 40 | 30 | 2262 | 99 | 74,20,6 |
| 24 | | 2:1 | 41 | 30 | 1955 | 98 | 83,14,3 |
| 25 | | 3:1 | 40 | 60 | 1586 | 99 | 90,8,2 |
| 26 | | 4:1 | 40 | 60 | 1328 | 99 | 92,7,1 |
| 27 | | 5:1 | 40 | 60 | 1005 | 99 | 92,7,1 |
| 28 | | 6:1 | 40 | 60 | 866 | 99 | 93,6,1 |

[a]Molar ratio of phosphine compound to anhydrous cobalt(III) acetylacetonate.
[b]TPP is triphenylphosophine.
[c]TCP is tricyclohexylphosphine.
[d]TBP is tri-n-butylphosphine.

Note from Table II that run 10, using no phoshpine compound, resulted in a significantly higher productivity but lower selectivity to 1-butene as compared to the runs of Example I using cobalt(II) acetylacetonate. The results of Table II further demonstrate that addition of a phosphine compound generally increases selectivity to 1-butene but decreases productivity (runs 11–28 as compared to run 10), and that increasing the amount of the phosphine compound further increases selectivity to 1-butene and further decreases productivity (runs 11–16, 17–22 and 23–28).

That which is claimed is:

1. A process for dimerizing ethylene to butenes consisting essentially of: contacting ethylene; a cobalt compound selected from the group consisting of an organocobalt(II) compound and an organocobalt(III) compound; and a borohydride compound of the formula MBH$_{4-n}$R$_n$ where n=1, 2, or 3, M is an alkali metal, and each R independently represents a C$_1$ to C$_{20}$ hydrocarbyl radical; wherein the ethylene is in a gaseous phase and the cobalt compound and borohydride compound are in a solvent and in a liquid phase, thereby producing a product reaction mixture in a liquid phase comprising said butenes.

2. A process as recited in claim 1 wherein the process is carried out at a pressure of about 5 to about 5000 psig, at a temperature of about 0° C. to about 125° C., and for a time of about 1 minute to about 15 hours.

3. A process as recited in claim 2 wherein the process is carried out at a pressure of about 200 to about 1000 psig, at a temperature of about 20° C. to about 50° C., and for a time of about 15 minutes to about 5 hours.

4. A process as recited in claim 1 wherein the cobalt compound is essentially anhydrous.

5. A process as recited in claim 1 wherein the cobalt compound is an organocobalt(II) compound.

6. A process as recited in claim 5 wherein the organocobalt(II) compound is selected from the group consisting of bis(cyclopentadienyl) cobalt(II) and cobalt(II) acetylacetonate.

7. A process as recited in claim 6 wherein the organocobalt(II) compound is cobalt(II) acetylacetonate.

8. A process as recited in claim 5 wherein the molar ratio of the borohydride compound to the organocobalt(II) compound is about 1-10 to 1.

9. A process as recited in claim 1 wherein the cobalt compound is an organocobalt(III) compound.

10. A process as recited in claim 9 wherein the organocobalt(III) compound is cobalt(III) acetylacetonate.

11. A process as recited in claim 9 wherein the molar ratio of the borohydride compound to the organocobalt(III) compound is about 2-10 to 1.

12. A process as recited in claim 9 wherein the molar ratio of the phosphine compound to the organocobalt(III) compound is about 0.1-20 to 1.

13. A process as recited in claim 1 wherein in the borohydride compound of the formula $MBH_{4-n}R_n$, $n=3$ and R is a $C_1$ to $C_{12}$ alkyl radical.

14. A process as recited in claim 13 wherein the borohydride compound is sodium triethylborohydride.

15. A process as recited in claim 1 wherein the solvent is selected from the group consisting of: at least one saturated hydrocarbon of the formula $C_nH_{2n+2}$ where $n=4, 5, 6, 7$ or 8; at least one aromatic hydrocarbon of the formula $C_6H_{6-n}(R'')_n$ where $n=0, 1, 2, 3$ or 4 and each R'' independently represents a $C_1$ to $C_6$ alkyl radical; and mixtures thereof.

16. A process as recited in claim 15 wherein the solvent is said at least one aromatic hydrocarbon.

17. A process for dimerizing ethylene to butenes consisting essentially of: contacting ethylene; an organocobalt(III) compound; a borohydride compound of the formula $MBH_{4-n}R_n$ where $n=1, 2,$ or 3, M is an alkali metal, and each R independently represents a $C_1$ to $C_{20}$ hydrocarbyl radical; and a phosphine compound of the formula $PR'_3$, where R' independently represents H or a $C_1$ to $C_{20}$ hydrocarbyl radical and where at least one R' is not H; wherein the ethylene is in a gaseous phase and organocobalt(III) compound, the borohydride compound, and the phosphine compound are in a solvent and in a liquid phase, thereby producing a product reaction mixture in a liquid phase comprising said butenes.

18. A process for dimerizing ethylene to butenes consisting of: contacting ethylene; a cobalt compound selected from the group consisting of an organocobalt(II) compound and an organocobalt(III) compound; and a borohydride compound of the formula $MBH_{4-n}R_n$ where $n=1, 2,$ or 3, M is an alkali metal, and each R independently represents a $C_1$ to $C_{20}$ hydrocarbyl radical; wherein the ethylene is in a gaseous phase and the cobalt compound and borohydride compound are in a solvent and in a liquid phase, thereby producing a product reaction mixture in a liquid phase comprising said butenes which comprise predominantly 1-butene.

19. A process for dimerizing ethylene to butenes consisting of: contacting ethylene; an organocobalt(III) compound; a borohydride compound of the formula $MBH_{4-n}R_n$ where $n=1, 2,$ or 3, M is an alkali metal, and each R independently represents a $C_1$ to $C_{20}$ hydrocarbyl radical; and a phosphine compound of the formula $PR'_3$ where R' independently represents H or a $C_1$ to $C_{20}$ hydrocarbyl radical and where at least one R' is not H; wherein the ethylene is in a gaseous phase and the organocobalt(III) compound, the borohydride compound, and the phosphine compound are in a solvent and in a liquid phase, thereby producing a product reaction mixture in a liquid phase comprising said butenes which comprise predominantly 1-butene.

* * * * *